(12) United States Patent
Roeder

(10) Patent No.: US 11,813,478 B2
(45) Date of Patent: Nov. 14, 2023

(54) BRACHYTHERAPY APPARATUS AND BRACHYTHERAPY METHOD

(71) Applicant: Carl Zeiss Meditec AG, Jena (DE)

(72) Inventor: Norman Roeder, Doebritschen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 17/039,381

(22) Filed: Sep. 30, 2020

(65) Prior Publication Data
US 2021/0093890 A1 Apr. 1, 2021

(30) Foreign Application Priority Data
Sep. 30, 2019 (DE) ...................... 10 2019 126 326.3

(51) Int. Cl.
*A61N 5/10* (2006.01)

(52) U.S. Cl.
CPC ......... *A61N 5/1007* (2013.01); *A61N 5/1049* (2013.01)

(58) Field of Classification Search
CPC .. A61N 5/1007; A61N 5/1049; A61N 5/1064; A61N 5/1014–1016; A61N 5/1002; A61N 2005/1003–1005; A61N 5/1001–1029; A61B 5/1076
See application file for complete search history.

(56) References Cited

U.S. PATENT DOCUMENTS

| | | | |
|---|---|---|---|
| 7,354,391 | B2 | 4/2008 | Stubbs |
| 7,497,819 | B2 | 3/2009 | White et al. |
| 7,497,820 | B2 | 3/2009 | White et al. |
| 7,524,274 | B2 | 4/2009 | Patrick et al. |
| 8,360,950 | B2 | 1/2013 | Acosta et al. |
| 9,101,395 | B2 | 8/2015 | Gutierrez et al. |

(Continued)

FOREIGN PATENT DOCUMENTS

| | | |
|---|---|---|
| CN | 1901969 A | 1/2007 |
| CN | 1929891 A | 3/2007 |

(Continued)

OTHER PUBLICATIONS

Office Action dated Sep. 2, 2021 issued in Chinese counterpart application No. CN 202011044884.2 and English-language translation thereof.

(Continued)

*Primary Examiner* — Thaddeus B Cox
(74) *Attorney, Agent, or Firm* — Ewers IP Law PLLC; Falk Ewers

(57) ABSTRACT

A brachytherapy apparatus and a brachytherapy method using the brachytherapy apparatus are provided. The brachytherapy apparatus includes a rod-shaped main element, a first holder, a second holder, side elements which extend between the first holder and the second holder and which are flexible and connected to the first holder and the second holder in such a way that a change in the relative position of the first holder in relation to the second holder brings about a change in the distance between the main element and the at least one side element, and a measuring apparatus configured to specify a measurement value based on at least one coordinate of the relative position of the first holder in relation to the second holder, said measurement value representing a quantity that depends on the distance.

21 Claims, 3 Drawing Sheets

(56) References Cited

U.S. PATENT DOCUMENTS

| | | | |
|---|---|---|---|
| 9,662,511 B2 | 5/2017 | Krechting | |
| 2005/0080313 A1 | 4/2005 | Stewart et al. | |
| 2006/0094923 A1 | 5/2006 | Mate | |
| 2007/0270627 A1* | 11/2007 | Cutrer | A61N 5/1015 600/7 |
| 2008/0091055 A1 | 4/2008 | Nguyen et al. | |
| 2009/0156882 A1 | 6/2009 | Chi Sing et al. | |
| 2010/0048978 A1 | 2/2010 | Sing et al. | |
| 2010/0234668 A1* | 9/2010 | Roeder | A61N 5/1014 600/3 |
| 2010/0331601 A1 | 12/2010 | Partridge et al. | |
| 2011/0230700 A1 | 9/2011 | Sing et al. | |
| 2012/0108881 A1 | 5/2012 | Chi Sing et al. | |
| 2012/0259401 A1 | 10/2012 | Gerrans et al. | |
| 2014/0088413 A1 | 3/2014 | Von Bucsh et al. | |
| 2014/0257013 A1* | 9/2014 | D'Andrea | A61N 5/1071 600/2 |
| 2014/0257088 A1 | 9/2014 | D'Andrea | |
| 2016/0287901 A1* | 10/2016 | Dumaine | A61B 17/3403 |
| 2017/0056628 A1* | 3/2017 | Vetter | A61N 5/1002 |
| 2018/0271407 A1* | 9/2018 | Sastry | A61M 25/09 |

FOREIGN PATENT DOCUMENTS

| | | | |
|---|---|---|---|
| CN | 101959555 A | 1/2011 | |
| CN | 102076378 A | 5/2011 | |
| CN | 201921311 U | 8/2011 | |
| CN | 201921325 U | 8/2011 | |
| CN | 103596497 A | 2/2014 | |
| CN | 104983493 A | 10/2015 | |
| CN | 105120950 A | 12/2015 | |
| DE | 4003458 A1 | 8/1991 | |
| EP | 1682213 B1 | 11/2011 | |
| WO | 2008045812 A1 | 4/2008 | |
| WO | WO-2017161331 A1 * | 9/2017 | A61B 17/00234 |

OTHER PUBLICATIONS

German Office Action, with translation thereof, for corresponding DE application No. 10 2019 126 326.3 dated May 8, 2020.

Klimberg et al., "Alternatives to whole breast irradiation in early breast cancer" Chinese Clinical Oncology, vol. 5, No. 3, 2016, pp. 1-10.

Njeh et al., "Accelerated Partial Breast Irradiation (APBI): A review of available techniques"; Radiation Oncology 2010, 5:90, 2010, pp. 1-28.

Extended European Search Report dated Feb. 5, 2021 of European counterpart application No. EP20198334.3 and English language translation thereof.

Office Action issued in Chinese Patent Application No. CN 202011044884.2, dated Feb. 21, 2022 (from which this application claims priority) and English language translation thereof.

Office Action issued in Chinese counterpart application No. CN 202011044884.2, dated May 27, 2022 and English language translation thereof.

Office Action issued in Chinese counterpart application No. CN 202011044884.2, dated Mar. 3, 2023, and English language translation thereof.

* cited by examiner

BRACHYTHERAPY APPARATUS AND BRACHYTHERAPY METHOD

CROSS REFERENCE TO RELATED APPLICATIONS

This application claims priority to German patent application DE 10 2019 126 326.3, filed Sep. 30, 2019, the entire content of which is incorporated herein by reference.

TECHNICAL FIELD

The present disclosure relates to a brachytherapy apparatus and a brachytherapy method, in particular an electronic brachytherapy method.

BACKGROUND

There are various established brachytherapy methods, which are performed with special brachytherapy radiation devices. In such brachytherapy methods, the aforementioned brachytherapy radiation devices are used to emit radiation, in particular x-ray radiation, in the interior of a human or animal body in the vicinity of tissue to be treated by therapy in order thereby to irradiate the tissue.

An exemplary brachytherapy radiation device includes a particle beam system which can generate a high energy particle beam. The particle beam is directed through a tube with a length of several centimeters which is part of the brachytherapy radiation device and directed at x-ray material arranged at the end of the tube. The interaction between the particle beam and the x-ray material causes the latter to generate x-ray radiation, which is provided to irradiate the tissue.

So that the x-ray radiation generated by the x-ray material at the end of the tube can be applied in the interior of the body, the tube is introduced into the body. To this end, the tube is surrounded by a rigid applicator that is placeable onto the brachytherapy radiation device, said applicator firstly representing a sterile barrier and secondly protecting the tube of the brachytherapy radiation device.

Irradiation with such a brachytherapy radiation device is usually performed following a resection of a tumor. As a result of the resection, a cavity arises in the body postsurgery, at the site where the tumor was previously located. Shape and size of the cavity differ from case to case and depend substantially on the shape and size of the removed tumor. For an efficient irradiation, it is advantageous if the shape and size of the employed applicator correspond to the shape and size of the cavity.

Since the cavity is located in the interior of the body and therefore not visible or not sufficiently visible from the outside, it is difficult in practice to determine a suitable applicator. Conventionally, the suitable applicator is ascertained by trial and error.

SUMMARY

It is therefore an object of the present disclosure to improve the procedure of selecting an applicator for a brachytherapy irradiation device which is used for irradiating matter surrounding a cavity.

The object is achieved by a brachytherapy apparatus and a brachytherapy method as described herein.

In particular, the object is achieved by a brachytherapy apparatus including a rod-shaped main element, the shape of which defines a longitudinal direction, a first holder fitted to the main element, a second holder fitted to the main element, at least one flexible side element which extends between the first holder and the second holder and which is connected to the first holder and the second holder in such a way that a change in the relative position of the first holder in relation to the second holder brings about a change of a distance between the main element and the at least one side element, as measured along a transverse direction that is oriented in orthogonal fashion with respect to the longitudinal direction; and a measuring apparatus which is configured to specify a measurement value on the basis of at least one coordinate of the relative position of the first holder in relation to the second holder, said measurement value representing a quantity that depends on the distance.

Without loss of generality, the assumption is made below that the brachytherapy apparatus includes a plurality of side elements. This only serves a simpler description. However, the brachytherapy apparatus only requires at least one side element.

The first holder is fitted to the main element. The first holder can be fitted to the main element in secured or movable fashion. If the first holder is fitted securely to the main element, the first holder cannot be moved relative to the main element. If the first holder is fitted to the main element in moveable fashion, the first holder can be moved relative to the main element, for example displaced along the longitudinal direction or rotated about the longitudinal direction. Further and other degrees of freedom of movement can be provided.

The second holder is fitted to the main element in moveable fashion. This means that the second holder can be moved relative to the main element, for example displaced along the longitudinal direction or rotated about the longitudinal direction. Further and other degrees of freedom of movement can be provided.

The first holder and the second holder are fitted to the main element in such a way that the first holder and the second holder are movable relative to one another according to at least one degree of freedom of movement. By way of example, the first holder and the second holder are fitted to the main element in such a way that the first holder and the second holder can be moved relative to one another along the longitudinal direction. By way of example, this is achieved by virtue of the first holder being securely fitted to the main element while the second holder is fitted to the main element so as to be displaceable along the longitudinal direction. Accordingly, the position of the second holder is variable along the longitudinal direction. Likewise, the distance between the first and second holder along the longitudinal direction is variable.

The first holder, the second holder and the side elements are functionally interconnected, more particularly mechanically interconnected, in such a way that a movement of the first holder in relation to the second holder according to the at least one degree of freedom of movement (i.e., a change in the relative position of the first holder in relation to the second holder according to the at least one degree of freedom of movement) brings about a change in the distance between the main element and the side elements and/or a change in the distance between the side elements. Accordingly, changing the relative position of the first holder in relation to the second holder according to the at least one degree of freedom of movement brings about a change of the width of the brachytherapy apparatus, as measured in the transverse direction. To simplify the description, the relative position of the first holder in relation to the second holder is also referred to as relative position only. Consequently, a change in the relative position can bring about a change in said distance and in said width.

The measuring apparatus serves to specify a measurement value that represents a quantity that is dependent on the distance. A quantity is dependent on the distance if a change in the distance leads to a change in the value of the quantity. By way of example, the measurement value can represent the distance itself. However, the measurement value could also represent said width of the brachytherapy apparatus since the width of the brachytherapy apparatus is a quantity that depends on the distance. Alternatively, the measurement value could represent a volume quantity, area quantity or length quantity which depends on the distance. By way of example, the measurement value represents a volume, a cross-sectional area or a diameter of an imaginary sphere which is approximated by the side elements.

The measuring apparatus specifies the measurement value depending on (i.e., on the basis of) at least one coordinate of the relative position, the change of which brings about a change in the distance between the main element and the side elements (i.e., the distance between the main element and the side elements depends on the at least one coordinate of the relative position). A relative position is distinguished by six coordinates, specifically three coordinates for the position and three coordinates for the orientation. Said at least one coordinate of the relative position is used by the measurement apparatus as a basis serving to specify the measurement value. Said at least one coordinate of the relative position can be any selection of the six coordinates, wherein the distance between the main element and the side elements depends on at least one of the selected coordinates.

By way of example, the at least one coordinate of the relative position could be the position of the first or second holder in the longitudinal direction. Alternatively, the at least one coordinate of the relative position could be the distance between the first and second holder along the longitudinal direction. Further alternatively, the at least one coordinate of the relative position could be the angle of rotation about the longitudinal direction between the first holder and the second holder.

The applicability of the brachytherapy apparatus described above will become clear in conjunction with the brachytherapy method described below. The method assumes that a cavity is present in matter, in particular in a human or animal body, the surrounding tissue of which should be irradiated by radiation.

Initially, the size of the cavity is determined using the brachytherapy apparatus. To this end, the brachytherapy apparatus is firstly introduced into the cavity. To introduce the brachytherapy apparatus into the cavity, it is advantageous if the brachytherapy apparatus has the smallest possible width in the transverse direction. This can be achieved by virtue of adapting the relative position in such a way that the distance between the main element and the side elements, or the width of the brachytherapy apparatus dependent thereon, is minimized or at least reduced.

As soon as the brachytherapy apparatus is arranged in the cavity, the relative position is altered in such a way that the distance between the main element and the side elements, or the width of the brachytherapy apparatus, increases. In this way, the relative position is altered until the brachytherapy apparatus has adopted a width that is so large that it corresponds to the width of the cavity along the transverse direction. In this state, the width of the brachytherapy apparatus approximately corresponds to the width of the cavity. Consequently, the width of the brachytherapy apparatus or the distance between the main element and the side elements is a measure for the size of the cavity.

This measure for the size of the cavity is represented by the measurement value which is specified by the measuring apparatus. Consequently, the measurement value specified by the measuring apparatus can represent the size of the cavity. By detecting the measurement value, it is possible to determine the size of the cavity.

After detecting the measurement value, the relative position can be altered anew, to be precise in such a way that the width of the brachytherapy apparatus is minimized or at least reduced. Consequently, the brachytherapy apparatus can easily be removed from the cavity.

For the purposes of irradiating the tissue surrounding the cavity which follows this, a suitable applicator is selected on the basis of the size of the cavity determined using the brachytherapy apparatus. The applicator selected thus is applied to a corresponding brachytherapy radiation device. The brachytherapy radiation device provided with the selected applicator is now introduced into the cavity. The irradiation is subsequently performed.

A substantial advantage of this method lies in the fact that a suitable size for the applicator can easily and quickly be determined with the brachytherapy apparatus. Therefore, it is not necessary to determine a suitable size for the applicator by trial and error or imprecise estimation methods.

BRIEF DESCRIPTION OF THE DRAWINGS

The disclosure will now be described with reference to the drawings wherein.

DESCRIPTION OF EXEMPLARY EMBODIMENTS

Figure 1A:
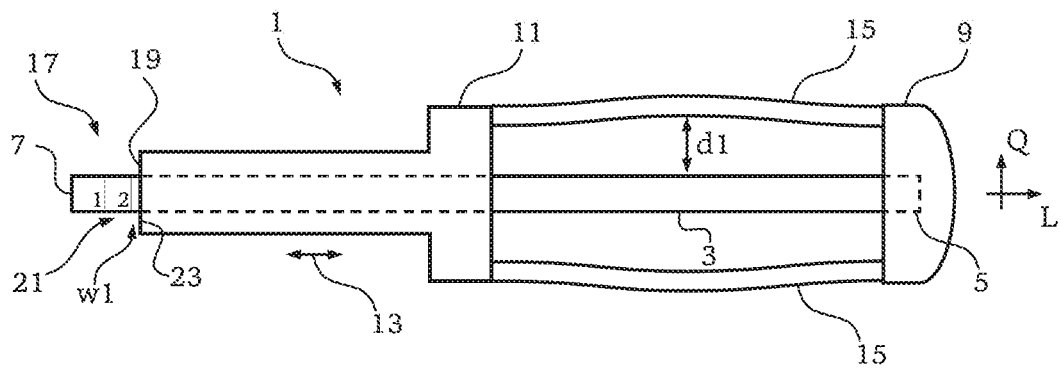
FIGS. 1A to 1C show a schematic illustration of a brachytherapy apparatus for different relative positions.
Figure 1B:
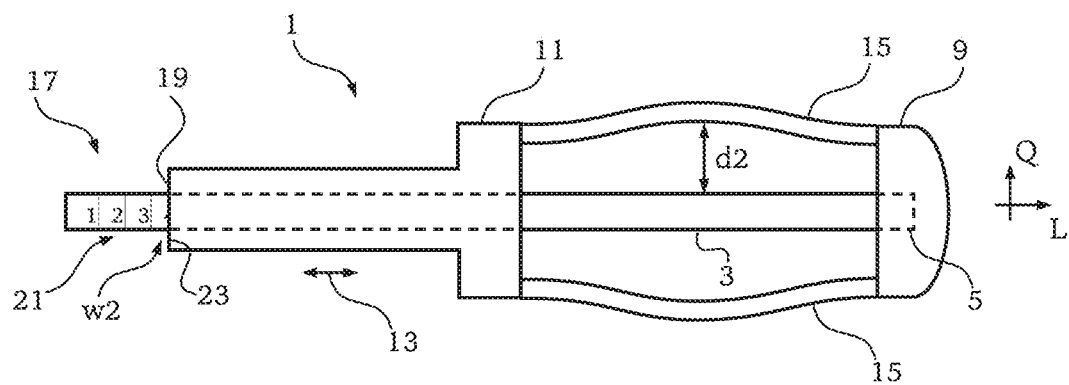
Figure 1C:
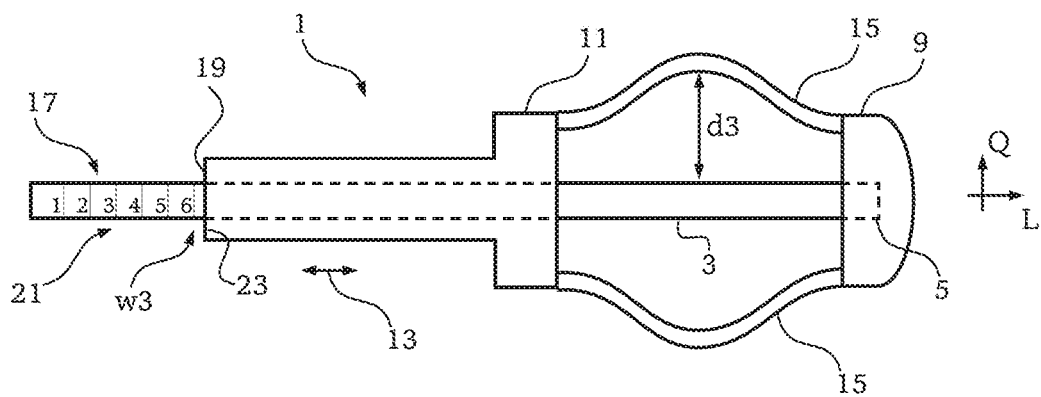

An exemplary brachytherapy apparatus 1 is described below with reference to FIGS. 1A to 1C. FIGS. 1A to 1C show a cross section through a brachytherapy apparatus 1 in a plane spanned by a longitudinal direction L and a transverse direction Q. The transverse direction Q is oriented in orthogonal fashion with respect to the longitudinal direction L.

The brachytherapy apparatus 1 includes a rod-shaped main element 3 with a front end 5 and a back end 7. The longitudinal direction extends in a straight line through the front end 5 and the back end 7 of the main element 3. By way of example, the main element 3 can have a circular or square cross section in a plane, the normal of which is the longitudinal direction L. Along the longitudinal direction L, the main element 3 can have a length of the order of 15 cm to 40 cm, for example. Along the transverse direction Q, the main element 3 can have a width of the order of 3 mm to 10 mm, for example. The specified numerical values only serve to specify a suitable order of magnitude. The main element 3 can be stiff, i.e., non-flexible and inextensible.

The brachytherapy apparatus 1 further includes a first holder 9, which is fitted to the main element 3. In the example shown in the figures, the first holder 9 is securely fitted to the front end 5 of the main element 3, and so the first holder 9 cannot be moved relative to the main element 3. By way of example, the first holder 9 is connected to the main element 3 by way of an adhesively bonded or screwed connection.

The brachytherapy apparatus 1 further includes a second holder 11, which is fitted to the main element 3. In the exemplary embodiment shown in the figures, the second holder 11 is fitted in movable fashion to the main element 3. More precisely, the second holder 11 is displaceable relative to the main element 3 along the longitudinal direction L, which is labelled by the double-headed arrow 13 in the figures. By way of example, this can be achieved by virtue of the fact that the main element 3 passes through the second holder 11 in a cutout formed in the second holder 11. In the exemplary embodiment explained with reference to FIGS. 1A to 1C, the position of the second holder 11 along the longitudinal direction L is a representative for the more general teaching of the relative position.

The brachytherapy apparatus 1 further includes two side elements 15. By way of example, the side elements 15 are flexible but inextensible strips or rods. The side elements 15 each extend between the first holder 9 and the second holder 11. The side elements 15 are arranged around the main element 3. Each of the side elements 15 is connected to both the first holder 9 and the second holder 11. The side elements 15 can be fastened to the first holder 9 and the second holder 11 in any desired way, for example by an interlocking connection, an adhesively bonded connection or the like. The side elements 15 can be adjustably fastened to the first holder 9 and/or the second holder 11 such that the length of the side elements 15 between the first holder 9 and the second holder 11 is variably adjustable. The side elements 15 can be connected to the first holder 9 and/or the second holder 11 in rigid or flexible fashion (e.g., by way of joints). The brachytherapy apparatus 1 can include more than two side elements 15 of this type.

The side elements 15 are attached to the first holder 9 and the second holder 11 in such a way that a change in the position of the second holder 11 along the longitudinal direction L (as a representative for the more general teaching of the change in the relative position according to one degree of freedom of movement) brings about a change of the distance between the main element 3 and the side elements 15 along the transverse direction Q.

FIG. 1A shows the brachytherapy apparatus 1 in a first state, in which the second holder 11 is relatively far away from the first holder 9 along the longitudinal direction L. In the case of this position of the second holder 11 along the longitudinal direction L, the distance between the main element 3 and the side elements 15 has a value d1.

FIG. 1B shows the brachytherapy apparatus 1 in a second state. In comparison with the first state shown in FIG. 1A, the second holder 11 is arranged closer to the first holder 9, which can be achieved, for example, by moving the second holder 11 in the direction of the first holder 9 along the longitudinal direction L. By moving the second holder 11 towards the first holder 9 (corresponding to a change in the relative position according to one degree of freedom of movement), a stress is caused in the side elements 15, causing the side elements 15 to deform since the side elements 15 are flexible and inextensible. Specifically, the side elements 15 are curved to the outside away from the main element 3, as a result of which the distance between the main element 3 and the side elements 15, as measured in the transverse direction Q, increases from the value d1 (see FIG. 1A) to the value d2 (see FIG. 1B). Consequently, the width of the brachytherapy apparatus 1, as measured in the transverse direction Q, has also increased.

FIG. 1C shows the brachytherapy apparatus 1 in a third state. In comparison with the second state shown in FIG. 1B, the second holder 11 is arranged even closer to the first holder 9, which can be achieved, for example, by moving the second holder 11 in the direction of the first holder 9 along the longitudinal direction L. Therefore, the side elements 15 have an even greater value d3 for the distance from the main element 3. Consequently, the width of the brachytherapy apparatus 1, as measured in the transverse direction Q, has also increased again.

The brachytherapy apparatus 1 further includes a measuring apparatus 17, which is configured to specify a measurement value w on the basis of the position of the second holder 11 along the longitudinal direction L (as a representative for the more general teaching of the at least one coordinate of the relative position), which measurement value represents a quantity dependent on the distance between the main element 3 and the side elements 15.

In the example shown in FIG. 1A to 1C, the measuring apparatus 17 includes a reading mark 19 and a scale 21. The reading mark 19 is formed by a back end 23 of the second holder 11. The scale 21 is located on the surface of the main element 3 and consists, for example, of a row of marks (e.g., lines) and a row of labels (e.g., numbers), which are assigned to the marks. The position of the reading mark 19 above the scale 21 depends on the position of the second holder 11 along the longitudinal direction L. This means that a change in the position of the second holder 11 along the longitudinal direction L leads to a change in the position of the reading mark 19 above the scale 21. The reading mark 19 specifies the measurement value on the scale 21.

FIG. 1A shows the brachytherapy apparatus 1 in the first state. The relative position of the first holder 9 in relation to the second holder 11, represented in the present case by the position of the second holder 11 along the longitudinal direction L, causes the distance d1 between the side elements 15 and the main element 3. For this position of the second holder 11 along the longitudinal direction L, the measuring apparatus 17 specifies a measurement value w1, which approximately has a value of 2 in FIG. 1A. The measurement value w1 represents a quantity that depends on the distance d1. By way of example, the measurement value w1 represents the width of the brachytherapy apparatus 1 along the transverse direction Q in units of centimeters. However, the measurement value could represent any desired defined quantity which depends on the distance between the side elements 15 and the main element 3 (i.e., any quantity whose value changes when the value of the distance varies).

FIG. 1B shows the brachytherapy apparatus 1 in the second state, in which the position of the second holder 11 along the longitudinal direction L has been altered as a result of a displacement of the second holder 11 towards the first holder 9, as a result of which the distance between the side elements 15 and the main element 3, as measured in the transverse direction Q, has the value d2, which is greater than the value d1. Accordingly, the measuring apparatus 17 specifies a different measurement value, specifically the measurement value w2, which approximately has a value of 4.

FIG. 1C shows the brachytherapy apparatus 1 in the third state, in which the position of the second holder 11 along the longitudinal direction L has been altered again by way of a further displacement of the second holder 11 towards the first holder 9. Accordingly, there has also been a change in the distance between the side elements 15 and the main element 3, as measured in the transverse direction Q, to the value d3, which is greater than the value d2. Accordingly, the measuring apparatus 17 now specifies a different measurement value yet again, specifically the measurement value w3, which approximately has a value of 6.

The configuration of the scale defines the meaning of the measurement value. According to the definition of the meaning of the measurement value, for example as the width of the brachytherapy apparatus 1 along the transverse direction Q, the scale can be determined experimentally, for example.

Figure 2:
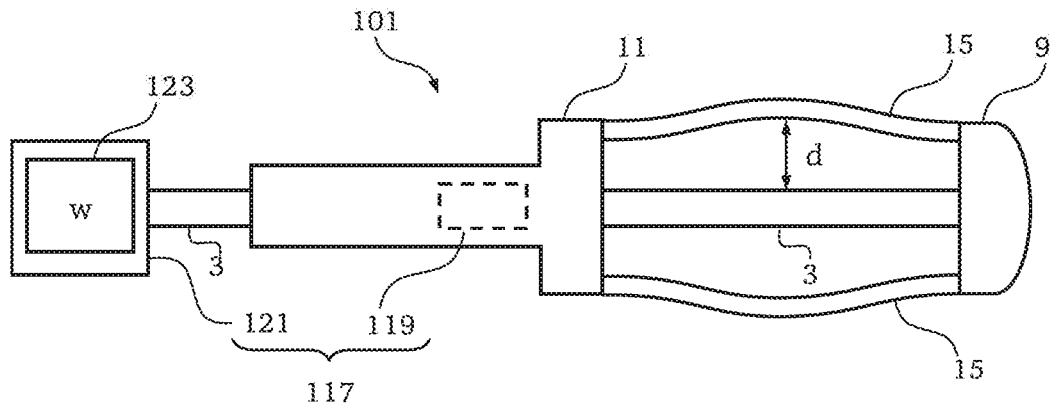
FIG. 2 shows a schematic illustration of a further brachytherapy apparatus.

FIG. 2 shows a schematic illustration of a further brachytherapy apparatus 101. The brachytherapy apparatus 101 largely corresponds to the brachytherapy apparatus 1, which was described above with reference to FIGS. 1A to 1C. The substantial difference between the brachytherapy apparatus 101 of FIG. 2 and the brachytherapy apparatus 1 of FIG. 1A to 1C is in the configuration of the measuring apparatus 117. The measuring apparatus 117 includes a sensor apparatus 119, which is configured to measure the position of the second holder 11 along the longitudinal direction L (as a representative for the more general teaching of the at least one coordinate of the relative position). A person skilled in the art is aware of numerous sensor apparatuses for determining the position of the second holder 11 along the longitudinal direction L. By way of example, the position can be implemented by measuring the distance between the second holder 11 and the first holder 9 with an interference measurement. Alternatively, the main element 3 could include a rack oriented along the longitudinal direction and the second holder 11 has a pinion engaging in the rack, with the rotational position of the pinion being measured and the position of the second holder 11 being determined on the basis thereof.

The measuring apparatus 117 further includes a controller 121 which is configured to determine and output the measurement value w on the basis of the position of the second holder 11 along the longitudinal direction L determined with the sensor apparatus 119. To output the measurement value w, the measuring apparatus 117 includes a display 123 which can display the measurement value w. The controller 121 and the display 123 are arranged at the back end of the main element 3.

The measuring apparatuses 17 and 117 described above are only examples of possible configurations of the measuring apparatus.

A brachytherapy method is explained below with reference to FIGS. 3A to 3C.

Figure 3A:
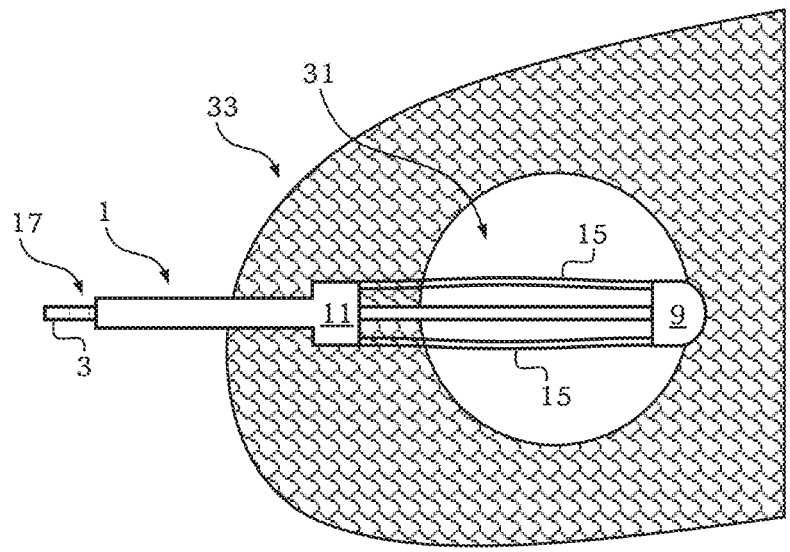
FIGS. 3A to 3C show schematically illustrated steps of a brachytherapy method using the brachytherapy apparatus shown in FIGS. 1A to 1C.
Figure 3B:
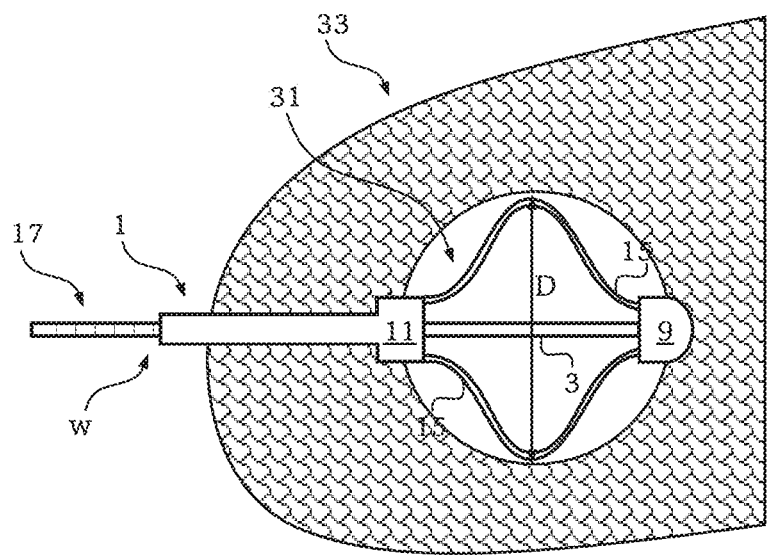
Figure 3C:
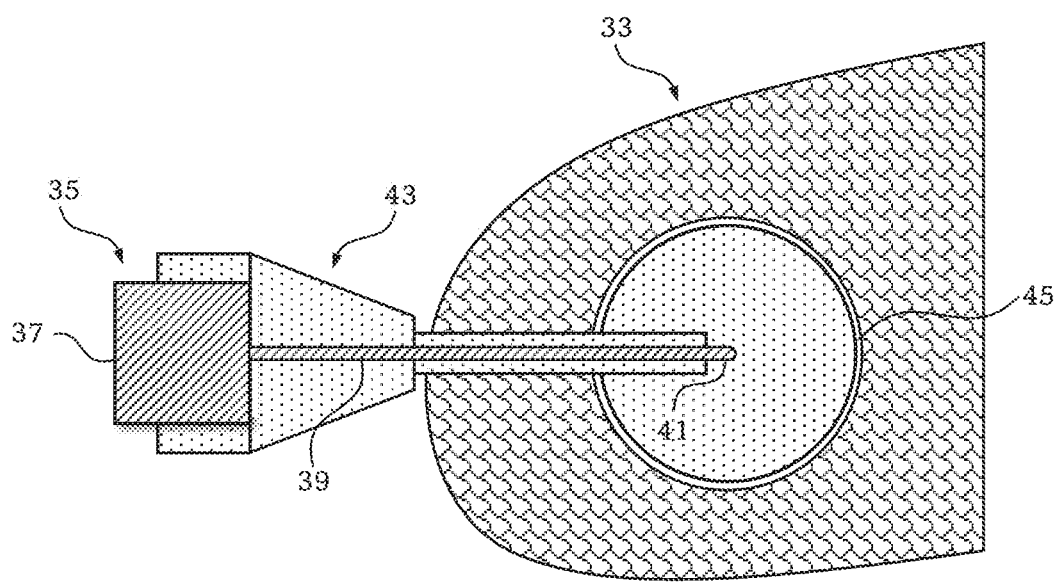

FIG. 3A shows a schematic illustration of a cavity 31 within matter 33 in a cross section. The matter 33 could be a human or animal body, for example. Through an aperture not illustrated in FIGS. 3A to 3C, a brachytherapy apparatus 1 (as a representative for any of the brachytherapy apparatuses described herein) is introduced into the cavity 31. To simplify the introduction into the cavity 31, the relative position is set in such a way that the width of the brachytherapy apparatus 1 is as small as possible, as illustrated in FIG. 3A.

As soon as the brachytherapy apparatus 1 has been introduced into the cavity 31, the size D of the cavity 31 is determined using the brachytherapy apparatus 1. As illustrated in FIG. 3B, the relative position is altered in such a way to this end that the side elements 15 reach the surface of the cavity 31. As a result, the side elements 15 approximate the size of the cavity 31. In this situation, the measurement value that can be read from the scale 21 (as a representative for the general teaching of the measurement value specified by the measuring apparatus) is a measure for the size D of the cavity 31. Consequently, the size D of the cavity 31 can be determined using the brachytherapy apparatus 1.

Then, the relative position can be altered again in such a way that the situation shown in FIG. 3A arises, in which the width of the brachytherapy apparatus 1 is minimized, and the brachytherapy apparatus 1 can be removed from the cavity 31 through the aperture, not illustrated here.

Subsequently, the matter 33 can be irradiated locally in the region of the cavity 31 using a brachytherapy radiation device 35. FIG. 3C illustrates such a brachytherapy radiation device 35.

In this exemplary embodiment, the brachytherapy radiation device 35 includes a main body 37 and a tube 39, at the end of which x-ray material 41 is arranged. A high-energy particle beam can be generated within the main body 37, which is directed at the x-ray material 41 through the tube 39, as a result of which x-ray radiation is generated.

To generate a predefined radiation profile and to protect the brachytherapy radiation device 35, an applicator 43 is placed on the brachytherapy radiation device 35 prior to the irradiation. The applicator 43 surrounds the tube 39 and has an applicator head 45 with a spherical outer shape, for example, at its front end. The applicator 43 is usually manufactured from rigid material and therefore has a rigid outer shape. Therefore, it is necessary to choose the shape and size of the applicator head 45 in such a way that these fit the shape and size of the cavity 31. Since the size D of the cavity 31 was already determined previously using the brachytherapy apparatus 1, a suitable applicator 43 can easily be chosen on the basis thereof. The applicator 43 selected in this manner can thereupon be placed onto the brachytherapy radiation device 35 and can be used with the latter to irradiate the regions of matter 33 surrounding the cavity 31.

The brachytherapy apparatus described above facilitates a simple determination of the size of a cavity. As a result of this, the selection of a suitable applicator can be simplified, and an incorrect selection can be avoided.

It is understood that the foregoing description is that of the exemplary embodiments of the disclosure and that various changes and modifications may be made thereto without departing from the spirit and scope of the disclosure as defined in the appended claims.

What is claimed is:

1. A measuring device for measuring a size of a cavity in the field of brachytherapy, the measuring device comprising:
    a rod-shaped main element, a shape of which defines a longitudinal direction;
    a first holder fitted to the rod-shaped main element;
    a second holder fitted to the rod-shaped main element;
    at least one flexible side element which extends between the first holder and the second holder and which is connected to the first holder and adjustably fastened to the second holder such that a length of the at least one flexible side element is variably adjustable, wherein the at least one flexible side element is bendable between the first holder and the second holder such that a change in a relative position of the first holder in relation to the second holder brings about a change of a distance between the rod-shaped main element and the at least one flexible side element, as measured along a transverse direction that is oriented in orthogonal fashion with respect to the longitudinal direction; and
    a measuring apparatus configured to specify a measurement value based on at least one coordinate of the relative position of the first holder in relation to the second holder, said measurement value representing a quantity that depends on the distance, and wherein the measurement value represents the size of the cavity.

2. The measuring device according to claim 1, wherein the measuring apparatus comprises a reading mark and a scale,
wherein a position of the reading mark on the scale depends on the at least one coordinate of the relative position of the first holder in relation to the second holder, and
wherein the reading mark specifies the measurement value on the scale.

3. The measuring device according to claim 1, wherein the measurement value represents a volume quantity, an area quantity, or a length quantity of the cavity which changes based on the distance between the rod-shaped main element and the at least one flexible side element.

4. The measuring device according to claim 1, wherein the measurement value represents a volume, a cross-sectional area, or a diameter of an imaginary sphere which is approximated by the at least one flexible side element.

5. The measuring device according to claim 1, wherein the rod-shaped main element is stiff, and/or
wherein the at least one flexible side element is inextensible.

6. The measuring device according to claim 1, further comprising:
a plurality of flexible side elements which extend between the first holder and the second holder, wherein each flexible side element is connected to the first holder and the second holder such that a change in the relative position of the first holder in relation to the second holder brings about a change of the distance between the rod-shaped main element and the respective flexible side element, as measured along the transverse direction.

7. The measuring device according to claim 6, wherein the plurality of flexible side elements are arranged around the rod-shaped main element.

8. The measuring device according to claim 1, wherein the first holder is securely fitted to the rod-shaped main element and the second holder is movable relative to the rod-shaped main element.

9. A brachytherapy system, comprising:
a measuring device according to claim 1 for measuring a size of a cavity in the field of brachytherapy;
a brachytherapy radiation device comprising a main body and a tube and configured to generate a high-energy particle beam in the main body and to direct the high-energy particle beam to an x-ray material arranged at an end of the tube; and
an applicator configured to be placed on the brachytherapy radiation device and to surround the tube,
wherein a size of the applicator is selected such that the applicator is suitable to irradiate regions of matter surrounding the cavity using the brachytherapy radiation device.

10. The measuring device according to claim 1, wherein the measuring apparatus comprises a sensor apparatus configured to measure the at least one coordinate of the relative position of the first holder in relation to the second holder, and
wherein the measuring apparatus further comprises a controller configured to determine and output the measurement value based on the at least one coordinate determined with the sensor apparatus.

11. The measuring device according to claim 1, wherein the at least one flexible side element is adjustably fastened to the second holder by joints.

12. A brachytherapy method, comprising:
determining a size of a cavity with a measuring device in the field of brachytherapy, the measuring device comprising a rod-shaped main element, a shape of which defines a longitudinal direction; a first holder fitted to the rod-shaped main element; a second holder fitted to the rod-shaped main element; at least one flexible side element which extends between the first holder and the second holder and which is connected to the first holder and the second holder such that a change in a relative position of the first holder in relation to the second holder brings about a change of a distance between the rod-shaped main element and the at least one flexible side element, as measured along a transverse direction that is oriented in orthogonal fashion with respect to the longitudinal direction; and a measuring apparatus configured to specify a measurement value based on at least one coordinate of the relative position of the first holder in relation to the second holder, said measurement value representing a quantity that depends on the distance;
selecting an applicator for a brachytherapy radiation device based on the determined size of the cavity, the applicator and the measurement device being separate devices; and
using the selected applicator for irradiating matter surrounding the cavity with the brachytherapy radiation device.

13. The brachytherapy method according to claim 12, wherein the applicator has a rigid outer shape.

14. A brachytherapy system, comprising:
measuring device for measuring a size of a cavity in the field of brachytherapy, the measuring device comprising:
a rod-shaped main element, a shape of which defines a longitudinal direction;
a first holder fitted to the rod-shaped main element;
a second holder fitted to the rod-shaped main element;
at least one flexible side element which extends between the first holder and the second holder and which is connected to the first holder and the second holder such that a change in a relative position of the first holder in relation to the second holder brings about a change of a distance between the rod-shaped main element and the at least one flexible side element, as measured along a transverse direction that is oriented in orthogonal fashion with respect to the longitudinal direction, wherein the at least one flexible side element is a rod;
a measuring apparatus configured to specify a measurement value based on at least one coordinate of the relative position of the first holder in relation to the second holder, said measurement value representing a quantity that depends on the distance;
a brachytherapy radiation device comprising a main body and a tube and configured to generate a high-energy particle beam in the main body and to direct the high-energy particle beam to an x-ray material arranged at an end of the tube; and
an applicator configured to be placed on the brachytherapy radiation device and to surround the tube, wherein a size of the applicator is selected such that the applicator is suitable to irradiate regions of matter surrounding the cavity using the brachytherapy radiation device.

15. The brachytherapy system according to claim 14, wherein the measuring apparatus comprises a reading mark and a scale,
   wherein a position of the reading mark on the scale depends on the at least one coordinate of the relative position of the first holder in relation to the second holder, and
   wherein the reading mark specifies the measurement value on the scale.

16. The brachytherapy system according to claim 14, wherein the measurement value represents a volume quantity, an area quantity, or a length quantity of the cavity which changes based on the distance between the rod-shaped main element and the at least one flexible side element.

17. The brachytherapy system according to claim 14, wherein the measurement value represents a volume, a cross-sectional area, or a diameter of an imaginary sphere which is approximated by the at least one flexible side element.

18. The brachytherapy system according to claim 14, wherein the rod-shaped main element is stiff, and/or
   wherein the at least one flexible side element is inextensible.

19. The brachytherapy system according to claim 14, further comprising:
   a plurality of flexible side elements which extend between the first holder and the second holder,
   wherein each flexible side element is connected to the first holder and the second holder such that a change in the relative position of the first holder in relation to the second holder brings about a change of the distance between the rod-shaped main element and the respective flexible side element, as measured along the transverse direction, and
   wherein each of the plurality of flexible side elements is a rod.

20. The brachytherapy system according to claim 19, wherein the plurality of flexible side elements are arranged around the rod-shaped main element.

21. The brachytherapy system according to claim 14, wherein the first holder is securely fitted to the rod-shaped main element and the second holder is movable relative to the rod-shaped main element.

* * * * *